United States Patent [19]

Kojima et al.

[11] Patent Number: 5,468,621
[45] Date of Patent: Nov. 21, 1995

[54] METHOD OF QUANTITATIVE ASSAY FOR 1,5-ANHYDROGLUCITOL

[75] Inventors: Ryo Kojima; Yoshiro Sato, both of Koriyama; Takeshi Nagasawa, Urawa, all of Japan

[73] Assignee: Nitto Boseki Co., Ltd., Fukushima, Japan

[21] Appl. No.: 21,250

[22] Filed: Feb. 23, 1993

[30] Foreign Application Priority Data

Mar. 2, 1992 [JP] Japan .................................. 4-044714

[51] Int. Cl.⁶ .............................. C12Q 1/26; C12Q 1/28
[52] U.S. Cl. .............................. 435/25; 435/14; 435/21; 435/28; 435/39; 435/962; 514/23
[58] Field of Search ............................ 435/25, 14, 21, 435/28, 39, 962; 514/23

[56] References Cited

U.S. PATENT DOCUMENTS

| | | | |
|---|---|---|---|
| 4,810,640 | 3/1989 | Nakamura et al. | 435/25 |
| 4,994,377 | 2/1991 | Nokamura et al. | 435/25 |

FOREIGN PATENT DOCUMENTS

| | | |
|---|---|---|
| 119332 | 9/1984 | European Pat. Off. . |
| 0261591 | 9/1987 | European Pat. Off. . |
| 58-43785 | 3/1983 | Japan . |
| 61-177986 | 8/1986 | Japan . |
| 61-239886 | 10/1986 | Japan . |
| 2-42980 | 2/1990 | Japan . |
| 2-104298 | 4/1990 | Japan . |

OTHER PUBLICATIONS

Hammerstedt et al, *The Journal of Biological Chemistry*, vol. 258, No. 14, pp. 8759–8768, Jul. 25, 1983.
Nakamura et al, *Chemical Abstracts*, vol. 114, p. 389, Ref. #243490m, 1991.
Pilkis et al, *Chemical Abstracts*, vol. 96, p. 323, Ref. #176865g, 1982 (Arch. Biochem. Biophys. 215(2), 379–389, 1982).
Fukumura et al, *Clinical Chemistry*, vol. 38, No. 12, pp. 2553–2554, 1992.
Yabuuchi et al, *Clinical Chemistry*, vol. 35, No. 10, pp. 2039–2043, 1989.
Fukumura, Yukihito et al., "Interference of Maltose for the Determination of 1,5–Anhydroglucitol with Lana AG$^\epsilon$ Kit", *Rhinsho Kagku (Nippon Rinsho Kagaki)*, 21 (1992), pp. 43–48.
Chemical Patents Index, Documentation Abstracts Journal D, Derwent Publications 1990; Nr. 90–161 279/21; J 02104298 A (Apr. 17, 1990).
Izumi et al.; Agric. Biol. Chem. 54 (6) 1393–1399 (1990).
Yoshioka et al., *J. Japan. Diab. Soc.* 25(10):1115–1118, 1982. Abstract only.

*Primary Examiner*—Michael G. Wityshyn
*Assistant Examiner*—Abdel A. Mohamed
*Attorney, Agent, or Firm*—Darby & Darby

[57] ABSTRACT

A quantitative assay for 1,5-anhydroglucitol in a specimen is described. This assay comprises treating a specimen with a phosphorylating enzyme in the presence of 5 to 500 mM adenosine-5'-triphosphate in a pH range of 7.2 to 8.5, to selectively eliminate sugars other than 1,5-anhydroglucitol, and reacting the product of this reaction, without removing the residual ATP, with pyranose oxidase in the above pH range. This assay is quite rapid and suitable for performance using an automated device.

7 Claims, 5 Drawing Sheets

CORRELATION TO COLUMN ENZYME METHOD

METHOD OF QUANTITATIVE ASSAY FOR 1,5-ANHYDROGLUCITOL

FIELD OF THE INVENTION

The present invention relates to a method of enzymatic assay for 1,5-anhydroglucitol (hereafter referred to as "1,5-AG"), which is expected as a marker for diagnosis of diabetes, in a simple and rapid way. This method is also applicable to an automated analysis device.

BACKGROUND OF THE INVENTION

RELATED ART STATEMENT 1,5-AG is a compound which is present in the cerebrospinal fluid and plasma of humans. It is reported that its quantity is markedly reduced in plasma collected from patients with certain diseases, particularly with diabetes (Yasuo Akanuma, Kazuyuki Tobe: Journal of Japanese Internal Medicine Association, 80, 1198–1204, 1991). 1,5-AG is thus expected to be as a marker for diagnosis of diabetes.

As assay for 1,5-AG, there are hitherto known a method based on gas chromatography (Yoshioka, Diabetes, 25, 1115–1118, 1982; hereafter referred to as "GC method") and methods using enzymes (hereafter referred to as "enzymatic methods") such as pyranose oxidase (hereafter abbreviated as PROD) or L-sorbose oxidase (Japanese Patent KOKAI (Laid-Open) No. 63-185397).

Serum or plasma collected from the patient with diabetes is mainly a specimen to be assayed for 1,5-AG. In blood from the patient with diabetes, its glucose concentration is higher than that of normal person. In blood from normal person, the glucose concentration is in the range of approximately 60 to 100 mg/dl, whereas in blood from the patient with diabetes, the glucose concentration is widely distributed in the range of 100 to 1000 mg/dl. On the other hand, the concentration of 1,5-AG in blood is in the range of 1.64 to 2.68 mg/dl for normal person but in the patient with diabetes its concentration is as extremely low as 0.18 to 0.21 mg/dl (Japanese Clinic, 47, 1989, extra issue, Immunological Inspection in Blood and Urinary Chemical Test over Wide Range; first volume, 439–442, Kawai). Therefore, the concentration of 1,5-AG in blood from the patient with diabetes becomes about 1/470 or less. In addition, glucose is structurally similar to 1,5-AG so that it is impossible to perform selective assay in the presence of 1,5-AG and glucose on the current technical level. It is thus essentially required to selectively remove glucose or pretreat specimen by adequately modifying the specimen.

In the GC method, the pretreatment requires removal of glucose and labeling of 1,5-AG which makes procedures complicate and involves analysis over long periods of time. For these reasons, it is difficult to assay a large number of specimens by the GC method. There are thus problems for applying the method to clinical assay.

In the enzymatic method, the pretreatment is performed by removing glucose using an ion exchange column or by modifying glucose through phosphorylation. The enzymatic method is accompanied by considerably complicated separation procedures when glucose is removed using an ion exchange column. Turning to glucose modification by phosphorylation, the optimum reaction conditions for phosphorylation including difference in the optimum pH were different from the optimum conditions for reactions of quantitative assay for 1,5-AG. Therefore, phosphorylation and assay for 1,5-AG must be carried out under different reaction conditions, respectively. In addition, adenosine-5'-triphosphate (hereafter referred to as "ATP") used for phosphorylation has an inhibitory action against PROD. In view of concentration, there is a limit in adding ATP to the assay system for accelerating phosphorylation and hence, it was difficult to terminate phosphorylation rapidly. In any event, it is impossible to perform quantitative assay rapidly by the prior art methods. In particular, any of the prior art methods has not come to be applied to an automated analysis device widely used for various clinical tests.

SUMMARY OF THE INVENTION

An object of the present invention is to eliminate the foregoing shortcomings of the prior art methods of assaying for 1,5-AG in a specimen described above and provide a method of quantitative assay for 1,5-AG in a simple and rapid manner without requiring separation procedures such as filtration, centrifugation, adsorption, etc.

Another object of the present invention is to provide a method of assay for 1,5-AG using an automated analysis equipment.

In order to solve the foregoing problems, the present inventor has made extensive investigations and as a result, found that the inhibitory action of ATP against PROD varies depending upon pH, and PROD is hardly inhibited by ATP at a pH value in the range of 7.2 to 8.5 and shows good reactivity with 1,5-AG. Therefore, by adopting such a method that PROD is acted on 1,5-AG in the pH range of 7.2 to 8.5, sugars in a specimen other than 1,5-AG can be removed by phosphorylation with hexokinase and ATP and in this case, the phosphorylation can be effected using an excess amount of ATP, whereby the reaction of 1,5-AG with PROD can be carried out subsequently to the phosphorylation. It has thus been succeeded in realizing the assay for 1,5-AG using an automated analysis device. The present invention has been so accomplished.

A first aspect of the present invention lies therefore in providing a method of quantitative assay for 1,5-AG in a specimen using PROD wherein PROD is reacted with 1,5-AG in a pH range of 7.2 to 8.5.

A second aspect of the present invention lies in providing a method of quantitative assay for 1,5-AG which comprises phosphorylating the sugars other than 1,5-AG in a specimen with hexokinase and an excess amount of ATP thereby to selectively remove the sugars so as to leave 1,5-AG in the specimen as it is, reacting PROD with 1,5-AG in the specimen in a pH range of 7.2 to 8.5 and quantitatively assaying 1,5-AG.

DETAILED DESCRIPTION OF PREFERRED EMBODIMENTS

Figure 1:
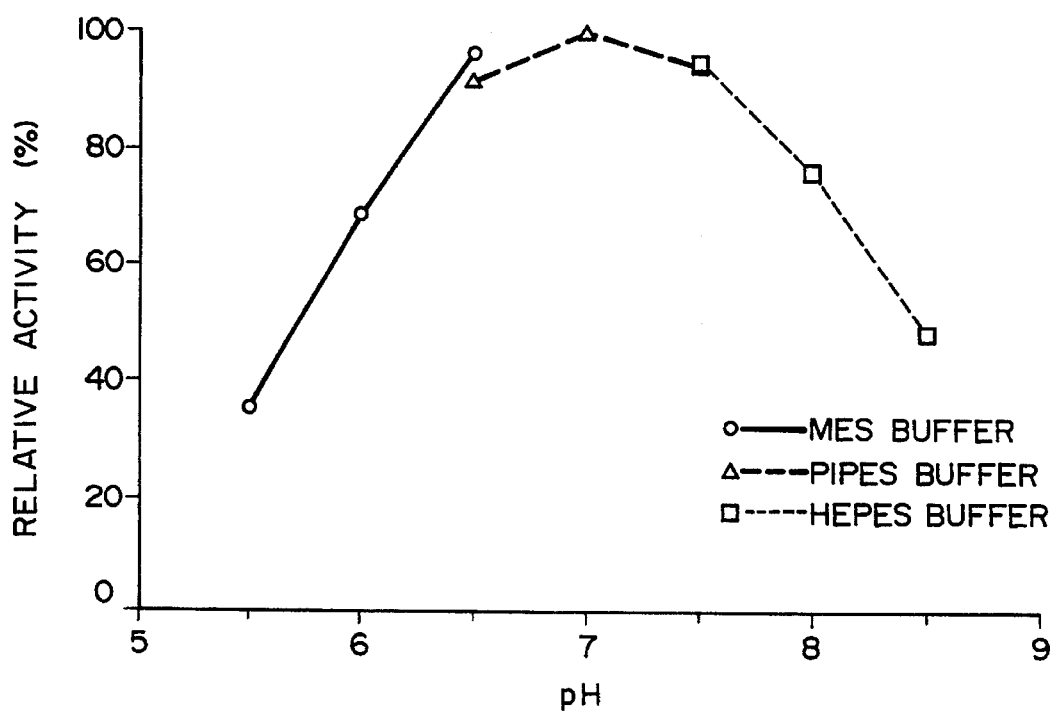
FIG. 1 shows the optimum pH of PROD for 1,5-AG in Good buffer solution.

Hereinafter the present invention will be described in detail.

The specimen in the present invention is used to mean any specimen; there is no particular restriction on PROD used so long as the PROD is classified as EC 1.1.3.10 according to Nomenclature of IUPAC-IUB. Examples of such specimen include blood, plasma, etc.

The PROD used in the present invention is a PROD derived from any microorganism capable of producing PROD. Typical examples of such PROD include PROD derived from the strains of microorganisms belonging to the genus Polyporus represented by *Polyporus obtusus* ATCC 26733 which is described in Japanese Patent KOKAI (Laid-Open) No. 61-239886, PROD derived from the strains of microorganisms belonging to the genus Coriolus represented by *Coriolus versicolor* IFO 4937 which is described in Japanese Patent KOKAI (Laid-Open) No. 58-43785, PROD derived from the strains of microorganisms belonging to the genus Pycnoporus represented by *Pycnoporus coccineus* IFO 4923 which is described in Japanese Patent KOKAI (Laid-Open) No. 62-79780, PROD derived from the strains of microorganisms belonging to the genus Basidiomycetous represented by *Basidiomycetous fungi* No. 52 (FERM P-10106) which is described in Japanese Patent KOKAI (Laid-Open) No. 2-42980, PROD derived from the strains of microorganisms belonging to the genus Daedaleopsis represented by *Daedaleopsis styracina* IFO 4910 which is described in Japanese Patent KOKAI (Laid-Open) No. 58-43785, PROD derived from the strains of microorganisms belonging to the genus Pleurotus represented by *Pleurotus ostreatus* Z-64 (NRRL 12507), PROD derived from the strains of microorganisms belonging to the genus Gloeophyllum represented by *Gloeophyllum sepiarium* Z-41 (NRRL 12506), PROD derived from the strains of microorganisms belonging to the genus Irpex represented by *Irpex lacteus* ATCC 20123 which is described in Japanese Patent KOKAI (Laid-Open) No. 61-177986, PROD derived from the strains of microorganisms belonging to the genus Pycnoporus represented by *Pycnoporus coccineus* IFO 4923, PROD derived from the strains of microorganisms belonging to the genus Auricularia represented by *Auricularia polytricha* Z-229 (FERM P-7119, PROD derived from the strains of microorganisms belonging to the genus Coprinus represented by *Coprinus micaceus* ATCC 20122, PROD derived from the strains of microorganisms belonging to the genus Trametes represented by *Trametes cinnabarinus* IFO 6139, etc.

Of these enzymes, preferred are PROD derived from the strains of microorganisms belonging to the genus Polyporus such as *Polyporus obtusus* ATCC 26733 and PROD derived from the strains of microorganisms belonging to the genus Basidiomycetes such as *Basidiomycetes fungi* No. 52, etc. PROD derived from the strains of microorganisms belonging to the genus Polyporus is particularly preferred.

In the present invention, PROD is acted on 1,5-AG in the pH range of 7.2 to 8.5. A particularly preferred pH range is between 7.5 and 8.0. By adopting the method in which 1,5-AG is reacted with PROD within such a pH range, PROD is hardly inhibited by ATP but shows good reactivity with 1,5-AG.

According to the present invention, therefore, the sugar other than 1,5-AG present in a specimen can be selectively removed in an extremely short period of time by phosphorylation using hexokinase and an excess amount of ATP in such a manner that 1,5-AG remains in the specimen and PROD can be reacted with 1,5-AG in the resulting specimen as it is, where 1,5-AG in the specimen can be quantitatively determined.

The sugars other than 1,5-AG in a specimen refer mainly to glucose but also include other sugars phosphorylated by hexokinase.

As the hexokinase which is used for phosphorylation of sugars other than 1,5-AG present in a specimen, including conversion of glucose into glucose-6-phopshate, it is preferred to use a hexokinase classified as EC 2.7.1.1 according to the classification defined by International Biochemical Association. In this conversion, ATP and magnesium ions are used together with the enzyme. As sources of magnesium ions there may be used organic acid salts such as magnesium fatty acid salts, magnesium acetate, etc., and inorganic acid salts such as halides, sulfates, nitrates, phosphates, etc. Among them, acetates and hydrochlorides are preferred.

The term "an excess amount of ATP" used in the phosphorylation described above refers to an amount of ATP generally in the range of 2.5 times moles or more, preferably 2.5 to 2,500 times moles, more preferably 10 to 1,000 times moles as much as an amount of glucose suspected to be contained in a sample. Practically, ATP is usually used in a determination system at an amount of 5 mM or more.

Preferred amounts of hexokinase, ATP and magnesium ions actually used in the reaction described above are in the range of 5 to 100 U/ml in hexokinase, in 5 to 500 mM of ATP and 5 to 50 mM of magnesium ions.

A preferred pH range for the phosphorylation is between 7.2 and 8.5 (inclusive) as in the reaction of 1,5-AG with PROD, with a more preferred range of 7.5 to 8.0.

In the present invention, phosphorylation can be carried out using an excess amount of ATP followed by enzymatic reaction of 1,5-AG in a specimen with PROD in the pH range of 7.2 to 8.5 as it is, without removing ATP. This enzymatic reaction is performed in the pH range of 7.2 to 8.5 so that PROD is not inhibited by ATP remained in the specimen but shows good reactivity with 1,5-AG. According to the present invention, therefore, the phosphorylation and the enzyme reaction can be continuously performed in a short period of time.

After sugars are selectively removed, 1,5-AG remained in a specimen is assayed by the action of PROD thereon. By reacting PROD with 1,5-AG, hydrogen peroxide generates. The hydrogen peroxide is acted on a known peroxidase substrate such as 2,2'-azinobis-(3-ethylbenzothiazoline-6-sulfonic acid), o-phenylenediamine, 5-aminosalicylic acid, 3,3',5,5'-tetramethylbenzidine, combination of 4-aminoantipyrine and N-ethyl-N-(2-hydroxysulfopropyl)-m-toluidine, using an enzyme classified as EC 1.11.1.7 according to the classification by International Biochemical Association. Absorbance of the dye thus produced from the substrate is measured.

The peroxidase used for determining hydrogen peroxide is preferably horse radish peroxidase. As the substrate used to produce the dye for measurement of absorbance, the combination of 4-aminoantipyrine and N-ethyl-N-(2-hydroxysulfopropyl)-m-toluidine is preferred. When using the combination of 4-aminoantipyrine and N-ethyl-N-(2-hydroxysulfopropyl)-m-toluidine, its wavelength in the absorbance measurement region is in the range of 500 nm to 800 nm. Within this range, two or more wavelengths may also be used for the measurement.

Preferred amounts of PROD, peroxidase, 4-aminoantipyrine and N-ethyl-N-(2-hydroxysulfopropyl)-m-toluidine used in the reaction described above are in the following ranges, respectively: 5 to 500 U/ml of PROD, 2 to 20 U/ml of peroxidase, 0.1 to 10 mM of 4-aminoantipyrine and 0.1 to 10 mM of N-ethyl-N-(2-hydroxysulfopropyl)-m-toluidine.

Throughout the reactions for assaying 1,5-AG in a specimen, the reaction temperature is maintained between 5° and 40° C., preferably between 25° and 40° C. The reaction time is 2 to 60 minutes, preferably 2 to 30 minutes. During the course of preparing the reaction solution, the reaction as a whole proceeds at pH of 7.2 to 8.5, preferably 7.5 to 8.0. Therefore, in order to stabilize the reaction solutions of reagents in the pH range of 7.2 to 8.5, preferably 7.5 to 8.0, phosphate buffer, Tris hydrochloride buffer, PIPES buffer, HEPES buffer, etc. are used as buffer solutions. When HEPES buffer is used, it is preferred to keep its concentration in the range of 50 to 500 mM. For controlling ionic intensity, halogenated alkali metal salts, preferably sodium chloride, etc. may be used.

Where 1,5-AG is assayed according to the method of the present invention, the respective components described above may be incorporated in one solution; alternatively, the respective components may also be used in appropriate combination. These components may be either in a solution form or freeze-dried. Where it is intended to store them over a long period of time, the components may preferably be freeze-dried. It is also possible to add a surface active agent within such a concentration range that does not inhibit the assay reaction. Where the measurement system is lyophilized, a stabilizer may be added in an appropriate amount.

In the present invention, the phosphorylation, enzymatic reaction and color-forming reaction subsequent thereto thereby to measure the amount of hydrogen peroxide generated can be performed using an automated analysis device.

The automated analysis device or equipment collectively termed in the present invention is specifically exemplified by Model 7050, Model 705, Model 736 and Model 7150 manufactured by Hitachi Ltd.; devices commercially available from Toshiba Co., Ltd., Hoffmann La Roche Co., Ltd., Bacster Co., Ltd., etc. The automated analysis device is not limited to these specific equipments but any devices equivalent thereto are usable in the present invention.

Hereafter the present invention is described in more detail with reference to the examples. Needless to say, the present invention is not deemed to be limited to these examples.

Example 1 Optimum pH of PROD to 1,5-AG

The optimum pH of PROD derived from *Polyporus obtusus* ATCC 26733 to 1,5-AG was determined. The results are shown in FIG. 1. The reaction conditions for the determination are as follows.

After 280 μl of the first reagent having the following composition and 70 μl of the second reagent having the following composition were added to 10 μl of 1000 U/l of PROD solution, the reaction was carried out. Change in absorbance was traced between 30 to 40 points for measurement at a main wavelength of 546 nm and a side wavelength of 700 nm, using automated analysis device, Hitachi Model 7150 by the function of the analysis device. A relative activity is shown when the maximum change in absorbance (when pH was 7.0) obtained was made 100%.

As shown in FIG. 1, PROD shows the highest activity for 1,5-AG in Good buffer solution such as MES, PIPES and HEPES in the pH range of 6.5 to 7.5.

| First Reagent: | |
|---|---|
| First reagent in the pH range of 5.5 to 6.5 | |
| MES | 200 mM |
| Sodium chloride | 150 mM |
| Magnesium acetate | 10 mM |
| N-Ethyl-N-(2-hydroxysulfopropyl)-m-toluidine | 1 mM |
| Peroxidase | 5 KU/l |
| Hexokinase | 20 KU/l |
| First reagent in the pH range of 6.5 to 7.5 | |
| PIPES | 200 mM |
| Sodium chloride | 150 mM |
| Magnesium acetate | 10 mM |
| N-Ethyl-N-(2-hydroxysulfopropyl)-m-toluidine | 1 mM |
| Peroxidase | 5 KU/l |
| Hexokinase | 20 KU/l |
| First reagent in the pH range of 7.5 to 8.5 | |
| HEPES | 200 mM |
| Sodium chloride | 150 mM |
| Magnesium acetate | 10 mM |
| N-Ethyl-N-(2-hydroxysulfopropyl)-m-toluidine | 1 mM |
| Peroxidase | 5 KU/l |
| Hexokinase | 20 KU/l |
| Second Reagent | |
| 4-Aminoantipyrine | 4 mM |
| Sodium chloride | 150 mM |
| 1,5-AG | 100 mM |
| Buffer | none |

Example 2 Change in pH of inhibition of PROD by ATP

The degree of the reaction of PROD derived from *Polyporus obtusus* ATCC 26733 with 1,5-AG affected by ATP was examined in Good buffer in the pH range of 5.5 to 8.5.

After 280 μl of the first reagent having the following composition and 70 μl of the second reagent having the following composition were added to 10 μl of 1000 U/l of PROD solution, the reaction was carried out. Change in absorbance was traced between 30 to 40 points for measurement at a main wavelength of 546 nm and a side wavelength of 700 nm, using automated analysis device, Hitachi Model 7150 by the function of the analysis device.

The inhibition degree by ATP is shown in terms of PROD activity as a relative activity where ATP was present in the same pH, when PROD activity was made 100% where ATP was absent under the conditions that 100 mM ATP was freshly added to buffer of each pH. The results obtained are shown in FIG. 2.

Figure 2:
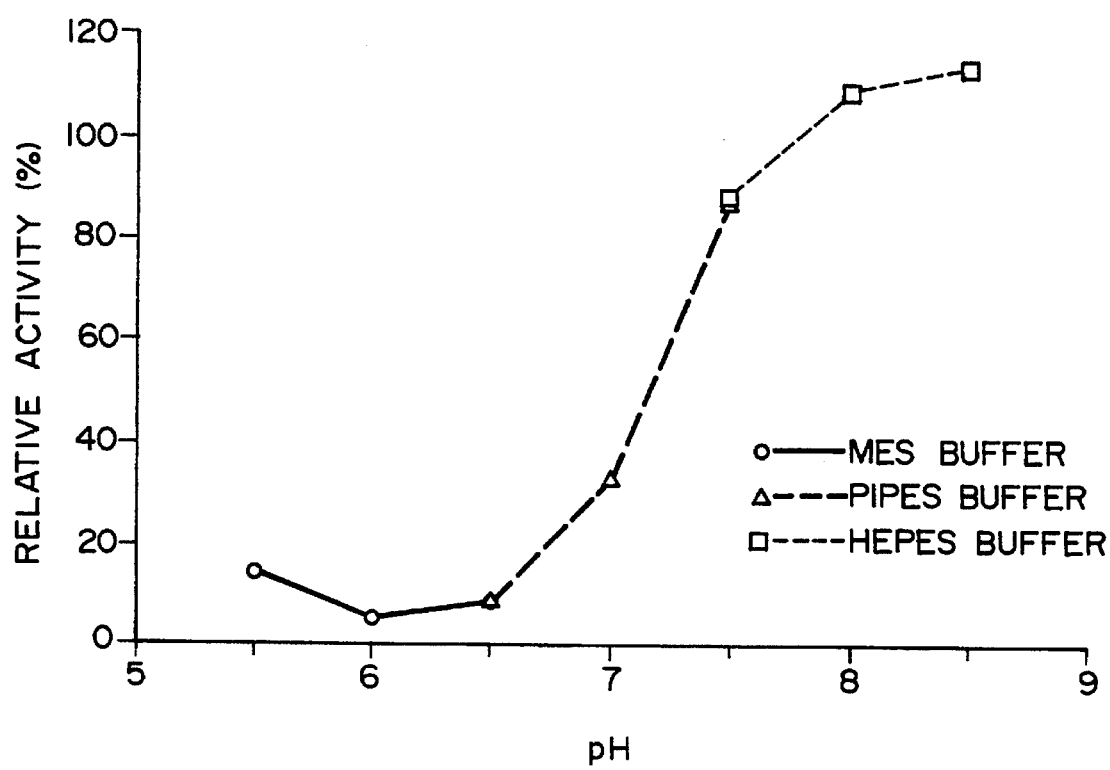
FIG. 2 shows a change with pH in inhibition of ATP against PROD.

As shown in FIG. 2, PROD was strongly affected by ATP at a pH of 7 or below but the degree of inhibition was markedly reduced at pH of 7.5 or above.

From the results shown in FIGS. 1 and 2, it is evident that PROD is hardly affected by ATP in the pH range of 7.5 to 8.0 but shows good reactivity with 1,5-AG.

| First Reagent: | |
|---|---|
| First reagent in the pH range of 5.5 to 6.5 | |
| MES | 200 mM |
| Sodium chloride | 150 mM |
| Magnesium acetate | 10 mM |

-continued

| | |
|---|---|
| N-Ethyl-N-(2-hydroxysulfopropyl)-m-toluidine | 1 mM |
| Peroxidase | 5 KU/l |
| Hexokinase | 20 KU/l |
| ATP | 0 mM or 100 mM |

First reagent in the pH range of 6.5 to 7.5

| | |
|---|---|
| PIPES | 200 mM |
| Sodium chloride | 150 mM |
| Magnesium acetate | 10 mM |
| N-Ethyl-N-(2-hydroxysulfopropyl)-m-toluidine | 1 mM |
| Peroxidase | 5 KU/l |
| Hexokinase | 20 KU/l |
| ATP | 0 mM or 100 mM |

First reagent in the pH range of 7.5 to 8.5

| | |
|---|---|
| HEPES | 200 mM |
| Sodium chloride | 150 mM |
| Magnesium acetate | 10 mM |
| N-Ethyl-N-(2-hydroxysulfopropyl)-m-toluidine | 1 mM |
| Peroxidase | 5 KU/l |
| Hexokinase | 20 KU/l |
| ATP | 0 mM or 100 mM |

Second Reagent

| | |
|---|---|
| 4-Aminoantipyrine | 4 mM |
| Sodium chloride | 150 mM |
| 1,5-AG | 100 mM |
| Buffer | none |

Example 3 Time course of measurement reaction in the present invention

Figure 3:
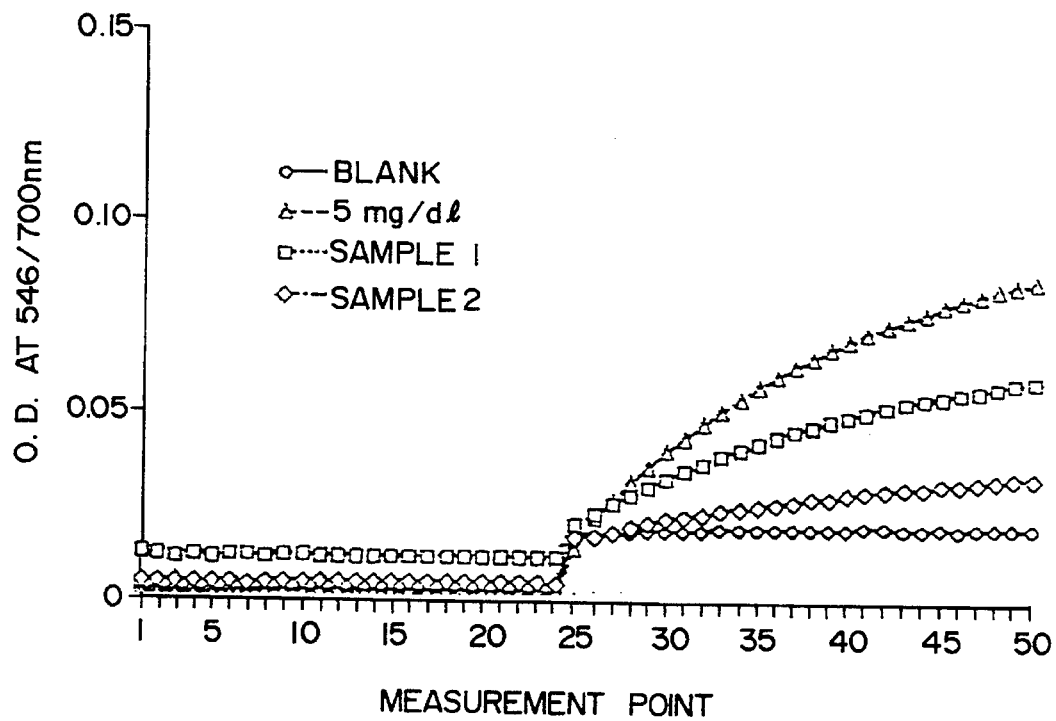
FIG. 3 shows time course for assay reaction in the present invention.

Physiological saline as blank control, 5 mg/dl of 1,5-AG aqueous solution and human serum were used as specimens. Each specimen was reacted with the first and second reagents having the following compositions, whereby reaction time course was measured. The results are shown in FIG. 3.

The reaction conditions are as follows: 7 μl of specimen, 280 μl of the first reagent and 70 μl of the second reagent were used and the assay was made at two points at main wavelength of 546 nm and side wavelength of 700 nm, using automated analysis device, Hitachi Model 7150. The measurement reaction was completed in almost 5 minutes.

| First Reagent: | |
|---|---|
| HEPES | 200 mM |
| Sodium chloride | 150 mM |
| Magnesium acetate | 10 mM |
| N-Ethyl-N-(2-hydroxysulfopropyl)-m-toluidine | 1 mM |
| Peroxidase | 5 KU/l |
| Hexokinase | 20 KU/l |
| ATP | 100 mM |
| pH 7.5 | |
| Second Reagent | |
| HEPES | 200 mM |
| Sodium chloride | 150 mM |
| 4-Aminoantipyrine | 4 mM |
| PROD | 62.5 KU/l |
| pH 7.5 | |

Example 4 Calibration curve of 1,5-AG and removal of glucose in specimen

Figure 4:
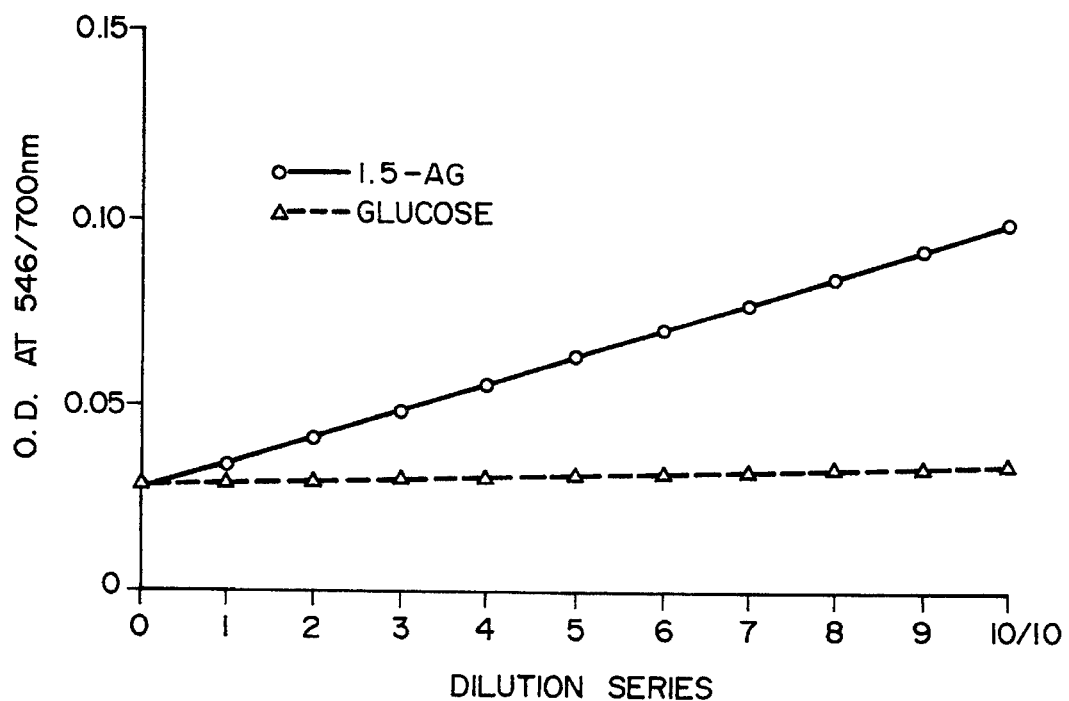
FIG. 4 shows a calibration curve of 1,5-AG and also shows glucose removal ability of the reaction system.

Under the measurement conditions of Example 3, 0 to 5 mg/dl of 1,5-AG aqueous solution prepared in concentration by 0.5 mg/dl difference was reacted and each absorbance was measured. The results are shown in FIG. 4. Furthermore, 0 to 1500 mg/dl of glucose aqueous solution prepared in concentration by 150 mg/dl difference was reacted in a similar manner and each absorbance was measured. The results are also shown in FIG. 4.

As is noted from FIG. 4, there was a satisfactory linearity up to 5 mg/dl which crosses the origin when 1,5-AG was reacted. Where glucose was reacted, almost the same absorbance as in reagent blank was obtained up to 1500 mg/dl, indicating that glucose was almost completely erased up to 1500 mg/dl. It can thus be judged that glucose was satisfactorily erased and good quantitative assay for 1,5-AG can be made under the measurement conditions in this Example.

Example 5 Test for recovery of 1,5-AG added

Using sera collected from patients with diabetes having known concentrations of 1,5-AG, 1,5-AG was added to these sera. Each of the thus obtained specimens was reacted under the conditions of Example 3 described above. 1,5-AG was quantitatively assayed using the calibration curve obtained in the foregoing Example.

The data actually obtained (amount found) was divided by the sum (theoretical amount) of the 1,5-AG content in the patient's serum and the amount of 1,5-AG added. The thus obtained value is made recovery rate. The results are shown in Table 1.

TABLE 1

Recovery Rate of 1,5-AG Added

| Serum from Patient (mg/dl) | Amount Added (mg/dl) | Theoretical Amount (mg/dl) | Amount Found (mg/dl) | Recovery Rate (%) |
|---|---|---|---|---|
| 0.36 | 1.24 | 1.60 | 1.70 | 106.3 |
| | 2.50 | 2.86 | 2.97 | 103.8 |
| 0.16 | 1.24 | 1.40 | 1.39 | 99.3 |
| | 2.50 | 2.66 | 2.59 | 99.3 |
| 0.35 | 1.24 | 1.59 | 1.65 | 103.8 |
| | 2.50 | 2.85 | 2.89 | 101.4 |
| 0.41 | 1.24 | 1.65 | 1.74 | 101.4 |
| | 2.50 | 2.91 | 2.97 | 102.1 |
| 0.49 | 1.24 | 1.73 | 1.79 | 103.5 |
| | 2.50 | 2.99 | 3.00 | 100.3 |
| | | | Average | 102.3 |

As is understood from Table 1, average recovery rate was almost 100%, indicating that the method of the present invention is highly accurate.

Example 6 Correlation with conventional method

Figure 5:
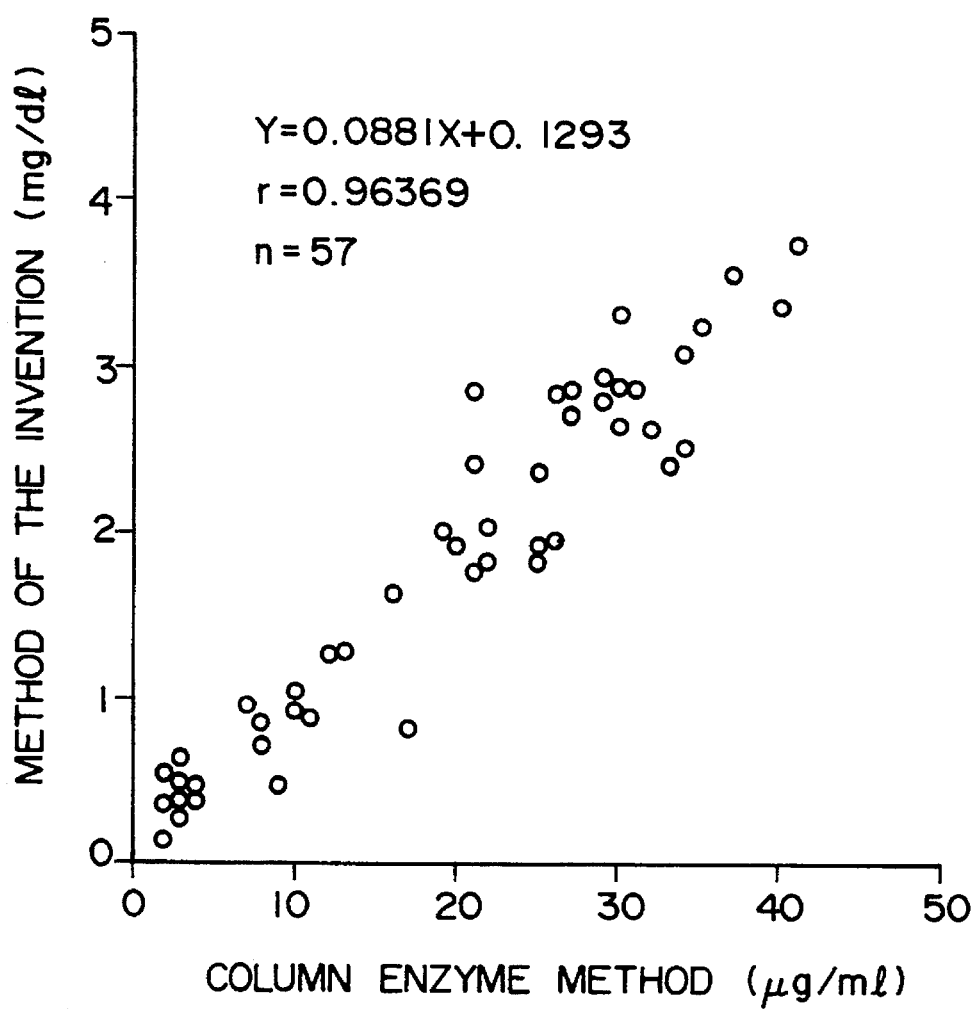
FIG. 5 shows correlation between the method of the present invention and the column enzyme method.

Correlation in measurement data of the enzymatic method of the present invention with conventional enzymatic method using ion exchange column which had been considered to be highly reliable method for quantitative determination of 1,5-AG (hereafter referred to as "column enzyme method") was examined. In the column enzyme method, 57 human serum specimens were assayed following the manual, using LANA AG (registered trademark) manufactured by Nippon Kayaku Co., Ltd. In the enzymatic method of the present invention, the same human sera as used in the column enzyme method were used as specimens and provided for quantitative assay in the same manner as in Example 3, using the calibration curve prepared in Example 4. The results are shown in FIG. 5. The correlation coefficient was 0.96 indicating that there was high correlation between the two methods.

As shown in the foregoing Examples, the method of quantitative assay for 1,5-AG according to the present invention is suited for applying to an automated analysis device. That is, according to the method of the present invention, 1,5-AG can be assayed using an automated device which could not be made by conventional methods. In addition, a large number of specimen can be handled rapidly and accurately also by assaying many clinical test items.

What is claimed is:

1. A quantitative assay for 1,5-anhydroglucitol which comprises:

A) treating a specimen with a phosphorylating enzyme in the presence of 5 to 500 mM adenosine-5'-triphosphate in a pH range of 7.2 to 8.5, to selectively eliminate sugars other than 1,5-anhydroglucitol and B) reacting the product of step A), without removing the residual ATP, with pyranose oxidase in the above pH range.

2. The assay of claim 1, wherein said pH range is 7.5 to 8.0.

3. The assay of claim 2, wherein said pyranose oxidase is derived from the microorganism *Polyporus obtusus*.

4. The assay of claim 2 including the additional step of:

C) measuring the hydrogen peroxide generated in step B).

5. The assay of claim 1, wherein said pyranose oxidase is derived from a microorganism of the genus Polyporus.

6. The assay of claim 5, wherein said microorganism is *Polyporus obtusus*.

7. The assay of claim 1 including the additional step of:

C) measuring the hydrogen peroxide generated in step B).

* * * * *